United States Patent [19]

Hamano et al.

[11] Patent Number: 4,764,006
[45] Date of Patent: Aug. 16, 1988

[54] OPHTHALMIC MEASURING APPARATUS

[75] Inventors: Yoshimasa Hamano; Takashi Masuda, both of Kawasaki, Japan

[73] Assignee: Canon Kabushiki Kaisha, Tokyo, Japan

[21] Appl. No.: 906,271

[22] Filed: Sep. 10, 1986

[30] Foreign Application Priority Data

Sep. 13, 1985 [JP] Japan ................................ 60-203027
Sep. 13, 1985 [JP] Japan ................................ 60-203028

[51] Int. Cl.⁴ ........................... A61B 3/10; A61B 8/10
[52] U.S. Cl. .................................. 351/211; 351/212; 128/660
[58] Field of Search ............... 351/208, 211, 212, 210, 351/247, 221; 128/660, 745

[56] References Cited

U.S. PATENT DOCUMENTS

| 3,821,891 | 7/1974 | Collins et al. | 351/211 |
| 4,227,780 | 10/1980 | Ohta et al. | 351/208 |
| 4,546,773 | 10/1985 | Kremer et al. | 128/660 |
| 4,598,714 | 7/1986 | Kremer et al. | 128/660 |

Primary Examiner—Rodney B. Bovernick
Assistant Examiner—Jay Ryan
Attorney, Agent, or Firm—Fitzpatrick, Cella, Harper and Scinto

[57] ABSTRACT

An ophthalmic measuring apparatus has an ultrasonic detector for measuring the length of a predetermined region of an eye to be examined, a device provided with a center axis coaxial with the center axis of the vibrator of the ultrasonic detector and projecting an index mark onto the cornea of the eye to be examined, and an imaging optical system for forming the corneal reflection image of the index mark on a predetermined image plane to measure the shape of the cornea.

15 Claims, 3 Drawing Sheets

OPHTHALMIC MEASURING APPARATUS

BACKGROUND OF THE INVENTION

1. Field of the Invention

This invention relates to an ophthalmic measuring apparatus, and more particularly to an ophthalmic measuring apparatus for effecting optical measurement of the shape of the cornea and measuring the lengths of various portions of an eye to be examined such as the thickness of the crystalline lens, the length of the vitreous body and the length of the eye axis by the use of an ultrasonic wave.

2. Related Background Art

Heretofore, spectacle lenses or contact lenses have been used for the correction of the refractive power of the eye after an operation for a cataract, but in recent years, it has become the practice to insert an in-the-eye lens into the position of the removed crystalline lens. To choose an in-the-eye lens proper for a patient having an eye having no crystalline lens, it becomes necessary to know the refractive power of the cornea and the length of the eye axis (the length from the cornea to the retina).

Heretofore, however, there has been the inconvenience that measurement of the refractive power of the cornea must be effected by a cornea shape measuring apparatus and measurement of the length of the eye axis must be effected by a separate ultrasonic measuring apparatus, whereafter the refractive power of the in-the-eye lens must be calculated. Also, much time has been required because alignment with the eye to be examined is effected by each of the measuring apparatuses.

SUMMARY OF THE INVENTION

It is an object of the present invention to eliminate the above-noted disadvantages peculiar to the prior art and to provide an ophthalmic measuring apparatus which can accomplish both the measurement of the shape of the cornea and measurement of the length of the eye axis.

It is also an object of the present invention to provide an ophthalmic measuring apparatus in which if alignment adjustment is effected by a cornea shape measuring system, the alignment adjustment by an eye axis length measuring system becomes unnecessary.

DESCRIPTION OF THE PREFERRED EMBODIMENTS

Figure 1:
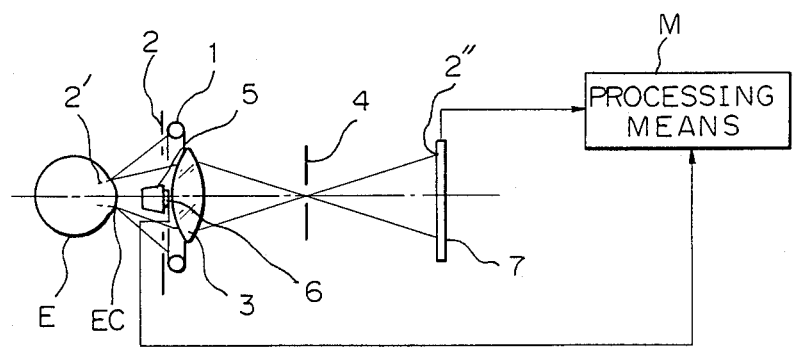
FIGS. 1 to 8 show various embodiments of the present invention.

FIG. 1 shows a first embodiment of the present invention. In FIG. 1, reference numeral 1 designates a ring-shaped light source and reference numeral 2 denotes a ring-shaped index mark. The ring-shaped index mark 2 is illuminated by the ring-shaped light source 1, and is projected onto the cornea Ec of an eye E to be examined and forms a corneal reflection image 2' which is a virtual image formed by corneal reflection.

The corneal reflection image 2' is re-imaged by an objective 3 whose optic axis is the center axis of the ring-shaped index mark 2, and the image of the index mark is formed on a light position detector 7 through a stop 4. The light from the corneal reflection image passes through the outer circumference of an ultrasonic wave conducting member 5 and of an ultrasonic vibrator 6.

The ring-shaped index mark 2 is a circular ring-shaped index mark, and as the radius of curvature of the cornea becomes smaller, the corneal reflection image becomes a circular ring-shaped image of smaller diameter, and if there is astigmatism in the cornea, the corneal reflection image will become elliptical.

The corneal reflection image on the light position detector 7 is generally elliptical, and by detecting the position coordinates of at least five points, an ellipse equation which is $ax^2+bxy+cy^2+dx+ey+1=0$ can be solved to thereby specify a—e, whereby the shape of the cornea is determined. This operation is accomplished by conventional processing means M such as a microcomputer.

The light position detector 7 is not restricted to the shown position, but may be at a position conjugate therewith.

A description will now be provided of an ultrasonic measuring system using an ultrasonic detector comprised of a vibrator and a medium section. The entire apparatus including the cornea shape measuring system and the ultrasonic measuring system is brought close to the eye to be examined, and the ultrasonic wave conducting member 5, which is the medium section, is brought into contact with the cornea Ec to thereby operate the ultrasonic vibrator 6 which lies forwardly of the objective 3, and the length of the eye axis, etc. are calculated from the measurement of the time required for the transmission and reception of an ultrasonic wave echo. The center axis of the ultrasonic vibrator 6 is coaxial with the center axis of the ring-shaped index mark 2 and in the present embodiment, it is also coaxial with the optic axis of the objective 3.

Figure 2:
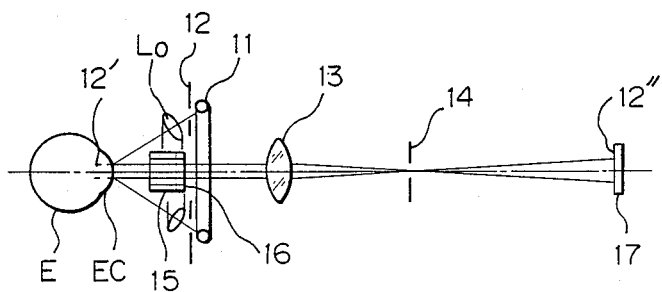

FIG. 2 shows a second embodiment of the present invention. Reference numeral 11 designates a ring-shaped light source, reference numeral 12 denotes a ring-shaped index mark, and reference numeral 13 designates an objective lens. The objective 13 has a rearward focus at the position of a stop 14 and is a telecentric optical system, and makes it difficult for the cornea shape measuring accuracy to be affected even if the working distance between the objective lens and the eye to be examined differs more or less from the original distance.

The index mark projecting system directly projects the ring-shaped index mark 12 onto the eye to be examined, but if a ring-shaped cylindrical lens $L_0$ whose rearward focus position is at the position of the ring-shaped index mark 12 ($L_0$ is a lens which has a refractive power in each meridian direction and has no refractive power in the circumferential direction) is provided between the eye to be examined and the ring-shaped index mark 12, the index mark will appear to be projected from infinity and therefore, coupled with the objective 13, the variation in the working distance will not affect the cornea shape measurement.

Now, in the present embodiment, an ultrasonic wave conducting member 15 and an ultrasonic vibrator 16 which together constitute an ultrasonic measuring system are cylindrical. In the case of the cornea shape measurement, the light from the corneal reflection image 12' passes through the hollow portion of the ultrasonic wave conducting member 15 which is the medium section and of the ultrasonic vibrator 16 and arrives at a light position detector 17 through an objective 13 and a stop 14.

The center axis of the ultrasonic vibrator 16 is coaxial with the center axis of the ring-shaped index mark 12 and is also coaxial with the optic axis of the objective 13.

In the above-described two embodiments, the ultrasonic vibrator is provided forwardly of the objective, that is, adjacent to the eye to be examined, but an aperture may be formed in the central portion of the objective and the ultrasonic vibrator may be contained in this aperture. Further, the ultrasonic vibrator in this aperture may be made integral with the objective.

Also, in the above-described two embodiments, the center axis of the ultrasonic vibrator has been described as being coaxial with the center axis of the ring-shaped index mark and with the optic axis of the objective, but cornea shape measurement can be accomplished even if the center axis of the ultrasonic vibrator is coaxial with the center axis of the ring-shaped index mark and the optic axis of the objective is parallel and eccentric to the center axis.

Figure 3:
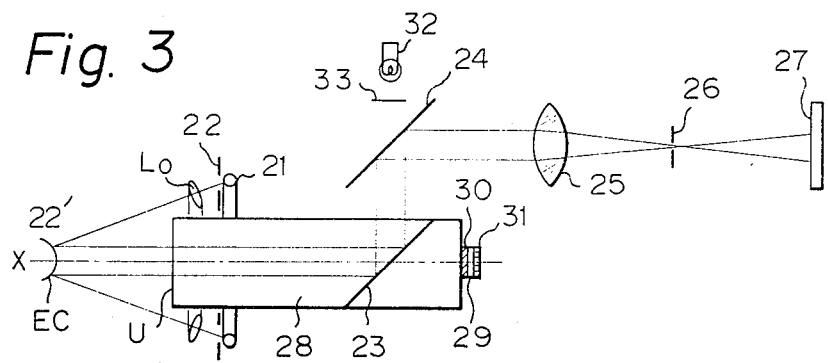

A description will now be provided of an embodiment in which at least a portion of the ultrasonic medium section is a light-transmitting member through which cornea shape measurement is effected. In FIG. 3, reference numeral 21 designates a ring-shaped light source, reference numeral 22 denotes a ring-shaped index mark, reference numeral 23 designates a light reflecting member, reference numeral 24 denotes a light dividing member, reference numeral 25 designates an imaging lens, reference numeral 26 denotes a stop, reference numeral 27 designates a light position detector, reference numeral 28 denotes a light-transmitting member (such as acryl or optical glass) capable of passing an ultrasonic wave therethrough, reference numeral 29 designates an ultrasonic vibrator, reference numeral 30 denotes an acoustic matching layer, reference numeral 31 designates an acoustic absorbing member, reference numeral 32 denotes a light source, and reference numeral 33 designates a fixation target.

The imaging lens 25 has a rearward focus at the position of the stop 26 and is a telecentric optical system, and makes it difficult for the cornea shape measurement accuracy to be affected even if the working distance between the imaging lens and the eye to be examined differs more or less from the original distance. The index mark projecting system directly projects the ring-shaped index mark 2 onto the eye to be examined, but if a ring-shaped cylindrical lens $L_0$ whose rearward focus is at the position of the ring-shaped index mark 2 is provided between the eye to be examined and the ring-shaped index mark 2, the index mark will appear to be projected from infinity and therefore, coupled with the imaging lens 25, the variation in the working distance will not affect the cornea shape measurement.

A description will now be provided of the cornea shape measuring system in the above-described construction. The ring-shaped light source 21 illuminates the ring-shaped index mark 22, and the ring-shaped index mark 22 is projected onto the cornea Ec of the eye to be examined, whereby a corneal reflection image 22', which is a virtual image, is formed.

The principal light ray from the corneal reflection image 22' emerges substantially in parallel to the measurement optic axis X and is imaged on the light position detector 27 such as a two-dimensional detecting element via the light reflecting member 23 and the light dividing member 24.

The ultrasonic measuring system will now be described. The light source 32 is turned on to illuminate the fixation target 33, and the ultrasonic detector comprising the light transmitting member 28 and the ultrasonic vibrator 29 is moved in the direction of the X-axis while the person to be measured is staring at the fixation target 33, and the surface V of the light transmitting member 28 is brought into contact with the cornea Ec of the eye to be examined.

The ultrasonic wave pulse emitted from the ultrasonic vibrator 29 is transmitted to the eye to be examined via the acoustic matching layer 30 and the light transmitting member 28, and the echo from the eye to be examined is received by the ultrasonic vibrator 29 via the light transmitting member 28 and the acoustic matching layer 30, whereby the length of the eye axis, etc. are calculated from the measurement of the time of the ultrasonic wave echo signal.

Figure 4:
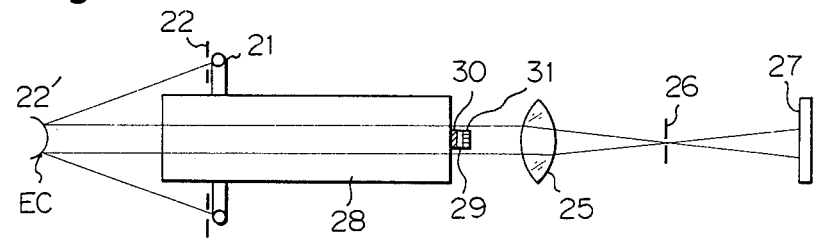

FIGS. 4 to 8 show different embodiments of the present invention. In the embodiment of FIG. 4, the corneal reflection image 22' of the ring-shaped index mark 22 passes the circumference of the ultrasonic vibrator 29 via the light transmitting member 28 and is imaged on the light position detector 27 by the imaging lens 25.

Figure 5:
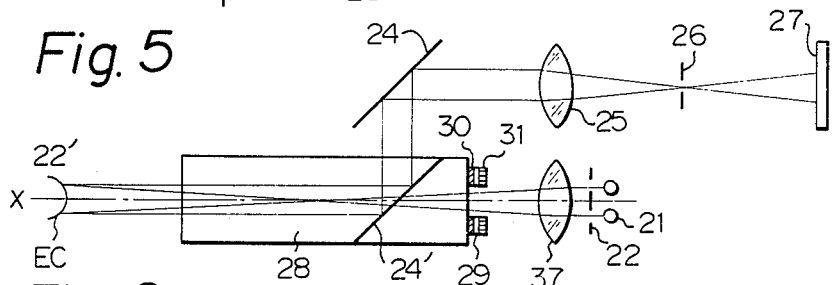

In the embodiment of FIG. 5, the vibrator 29 is provided in a ring-like shape about the X-axis, and the ring-shaped index mark 22 is projected onto the cornea Ec via a lens 37, the central opening of the vibrator 29 and the light transmitting member 28, and the corneal reflection image 22' thereof is imaged on the light position detector 27 by the imaging lens 25 via the light transmitting member 28 and the light dividing members 24 and 24'.

Figure 6:
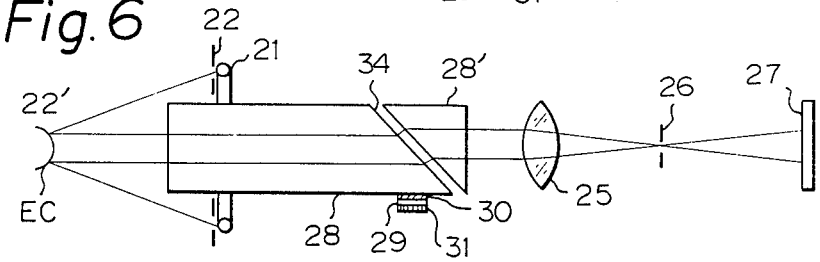

In the embodiment of FIG. 6, the corneal reflection image 22' of the ring-shaped index mark 22 is imaged on the light position detector 27 by the imaging lens 25 via the light transmitting members 28 and 28' while, on the other hand, the ultrasonic wave pulse from the ultrasonic vibrator 29 is transmitted and received through an ultrasonic wave reflecting surface 34.

Figure 7:
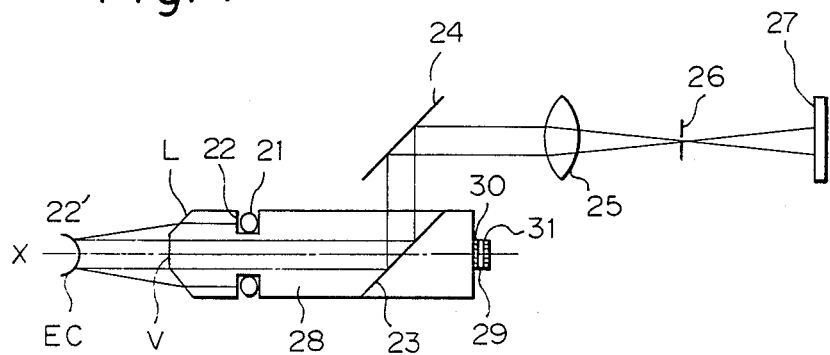

In the embodiment of FIG. 7, that surface of the ultrasonic wave detector comprising a light transmitting member and an ultrasonic vibrator which contacts the cornea comprises a circular flat surface V about the X-axis, and a surface L, having the function of a ring-shaped light deflecting means provided on the circumference thereof, and the ring-shaped light source 21 incorporated in the light transmitting member, illuminates the ring-shaped index mark 22 and the light is deflected by the surface L and imaged on the cornea Ec, and the corneal reflection image 22' is imaged on the light position detector 27 by the imaging lens 25 via the light transmitting member 28, the light reflecting member 23 and the light dividing member 24.

Figure 8:
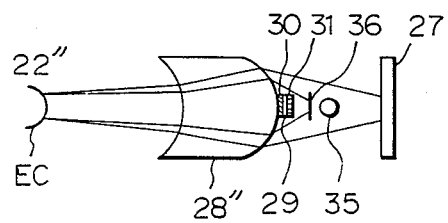

In the embodiment of FIG. 8, the ring-shaped index mark 36 is projected onto the cornea Ec via the light transmitting member 28" having the function of a lens, and the corneal reflection image 22" thereof is imaged on the light position detector 27 via the light transmitting member 28".

In the above-described embodiments, the area other than the area of the medium section of ultrasonic wave through which the cornea shape measuring light beam passes has also been considered as having the light transmitting property, but it is apparent that the area other than the area through which the cornea shape measuring light beam passes may be comprised of a light intercepting member or even the light transmitting member may have its end surface painted in black to provide a light intercepting property.

Also, in the above-described embodiments, it has been shown that the corneal reflection image is imaged on the light position detecting means provided on the image plane, by the imaging optical system, whereby cornea shape measurement can be automatized, but it is apparent that the corneal reflection image may be observed through a conventional finder system or monitor system which forms its point of focus on the image plane, thereby accomplishing cornea shape measurement.

What we claim is:

1. An ophthalmic measuring apparatus comprising:
   an ultrasonic detector adapted to be positioned on the cornea of an eye to be examined for determining the length of a predetermined region of the eye to be examined by calculating the length of the predetermined region based on measuring the time required for the transmission and reception of an ultrasonic wave echo, wherein said ultrasonic detector comprises a vibrator;
   an index means for projecting an index mark onto the cornea of the eye to be examined, wherein the center axis of said index means is coaxial with the center axis of said vibrator of said ultrasonic detector; and
   an imaging optical system positioned coaxially with said index means, for forming the corneal reflection image of said index mark on a predetermined image plane to measure the shape of the cornea.

2. An ophthalmic measuring apparatus according to claim 1, wherein at least a portion of a medium section of said ultrasonic detector is formed by a light transmitting member, and the corneal reflection image of said index mark is imaged on said image plane through said light transmitting member.

3. An ophthalmic measuring apparatus according to claim 2, provided with a fixation target presented to the eye to be examined through said light transmitting member.

4. An ophthalmic measuring apparatus according to claim 2, wherein a portion of said light transmitting member is provided with a light reflecting portion.

5. An ophthalmic measuring apparatus according to claim 2, wherein said vibrator is ring-shaped and said index mark is projected from the central opening in said vibrator onto the eye to be examined.

6. An ophthalmic measuring apparatus according to claim 2, wherein said index mark is provided at a position in said light transmitting member.

7. An ophthalmic measuring apparatus according to claim 6, wherein the end surface of said medium section which is adjacent to the eye to be examined is a light deflecting surface so that the light from said index mark emerges from said end surface and is deflected toward the eye to be examined.

8. An ophthalmic measuring apparatus according to claim 1, wherein light position detecting means is provided on said image plane.

9. An ophthalmic measuring apparatus according to claim 1, wherein said vibrator is provided on that side of said imaging optical system which is adjacent to the eye to be examined.

10. An ophthalmic measuring apparatus according to claim 1, wherein the corneal reflection image of said index mark passes around the outer side of said vibrator and is imaged on said image plane.

11. An ophthalmic measuring apparatus according to claim 1, wherein said vibrator is ring-shaped and the corneal reflection image of said index mark passes through the central opening in said vibrator and is imaged on said image plane.

12. An ophthalmic measuring apparatus according to claim 2, wherein said medium section is lens-like.

13. An ophthalmic measuring apparatus according to claim 2, wherein a portion of said medium section is provided with an ultrasonic wave reflecting surface.

14. An ophthalmic measuring apparatus according to claim 1, wherein said imaging optical system comprises an objective lens and a stop at a rearward focal plane of said objective lens, whereby said imaging optical system is a telecentric system.

15. An ophthalmic measuring apparatus according to claim 14, wherein said index means comprises a ring-shaped cylindrical lens.

* * * * *

UNITED STATES PATENT AND TRADEMARK OFFICE
CERTIFICATE OF CORRECTION

PATENT NO. : 4,764,006
DATED : August 16, 1988
INVENTOR(S) : YOSHIMASA HAMANO, ET AL.

It is certified that error appears in the above-identified patent and that said Letters Patent is hereby corrected as shown below:

COLUMN 2

Line 40, objective 13" should read --objective lens 13--.

COLUMN 3

Line 47, "mark 2" should read --mark 22--.
Line 49, "mark 2" should read --mark 22--.
Line 51, "mark 2," should read --mark 22,--.

COLUMN 4

Line 7, "surface V" should read --surface U--.

Signed and Sealed this

Eleventh Day of April, 1989

Attest:

DONALD J. QUIGG

*Attesting Officer*    *Commissioner of Patents and Trademarks*